(12) United States Patent
Spector et al.

(10) Patent No.: US 6,277,844 B1
(45) Date of Patent: Aug. 21, 2001

(54) COMPOUND FOR SELECTIVE TREATMENT OF MALIGNANT CELLS BY INHIBITING CELL CYCLE PROGRESSION, DECREASING BCL2, AND INCREASING APOPTOSIS

(76) Inventors: Sydney Spector, 600 Green Park, Nashville, TN (US) 37215; Neil L. Spector, 318 Sunset Creek Cir., Chapel Hill, NC (US) 27516

( * ) Notice: Subject to any disclaimer, the term of this patent is extended or adjusted under 35 U.S.C. 154(b) by 0 days.

(21) Appl. No.: 09/395,812

(22) Filed: Sep. 14, 1999

Related U.S. Application Data

(60) Provisional application No. 60/100,217, filed on Sep. 14, 1998.

(51) Int. Cl.[7] .................. C07D 487/04; A61K 31/55; A61P 35/00

(52) U.S. Cl. .................................. 514/215; 540/578

(58) Field of Search .................. 540/578; 514/215

(56) References Cited

U.S. PATENT DOCUMENTS

| | | | |
|---|---|---|---|
| 3,516,988 | 6/1970 | Schmitt | 260/239.3 |
| 3,965,151 | 6/1976 | Derieg | 260/490 |
| 3,996,209 | 12/1976 | Chase | 260/239.3 |
| 3,997,591 | 12/1976 | Derieg | 260/470 |
| 4,316,829 | 2/1982 | Gerecke | 260/239.3 |
| 4,377,522 | 3/1983 | Branca | 260/239.3 |
| 4,748,239 | 5/1988 | Floyd | 540/523 |
| 4,752,645 | 6/1988 | Das | 540/523 |
| 4,902,684 | 2/1990 | Floyd | 514/211 |
| 5,010,074 | 4/1991 | Gronwald | 514/213 |
| 5,556,969 | 9/1996 | Chambers | 540/509 |
| 5,597,915 | 1/1997 | Chambers | 540/509 |

OTHER PUBLICATIONS

Miller, D.M. "The Future of Oncology" in "Cecil Textbook of Medicine, 20th Edition", W.B. Saunders, Philadelphia, 1996, pp. 1071–1077.*

Salmon, S.E. et al "The Principles of Cancer Therapy" in "Cecil Textbook of Medicine, 20th Edition", W.B. Saunders, Philadelphia, 1996, pp. 1036–1049.*

Balasubramanian, B.N. et al, "Recent Developments in Cancer Cytoxics" in "Annual Reports in Medicinal Chemistry, vol. 33", Academic Press, San Diego, 1998, pp. 151–159.*

(List continued on next page.)

*Primary Examiner*—Mark L Berch
*Assistant Examiner*—Thomas McKenzie
(74) *Attorney, Agent, or Firm*—Waddey & Patterson; Michael J. McCarthy; Richard S. Myers, Jr.

(57) ABSTRACT

The invention provides compounds of the formula (I):

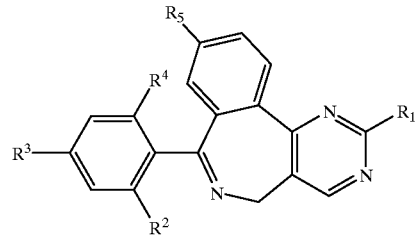

wherein $R_1$ is an amino or an alkyl group, optionally substituted with one or more groups selected from $C_1$–$C_6$ alkyl group; $R_2$ is H or halogen; $R_3$ is H, halogen, hydroxyl group, or alkyl group; $R_4$ is H or halogen; and $R_5$ is halogen, preferably chlorine; and salts and prodrugs thereof; and a method of using these compounds for the treatment of cancer.

27 Claims, 4 Drawing Sheets

OTHER PUBLICATIONS

Miller, D.K., "Regulation of Apoptosis of Members of the ICE Family and the Bcl–2 Family" in "Annual Reports in Medicinal Chemistry, vol. 31", Academic Press, San Diego, 1996, pp. 249–268.*

Oltersdorf, T. et al, "The Bcl–2 Family: Targets for the Regulation of Apoptosis" in "Annual Reports in Medicinal Chemistry, vol. 33", Academic Press, San Diego, 1998, pp. 253–262.*

Aldrich Chemical Company, Milwaukee, WI, 1192, p. 146, entry 86–165–0.*

Leif C. Anderson, et al. (1981), " Diazepam induces mitotic arrest at prometaphase by inhibiting centriolar seperation," Nature 291: 247–248.

Lynn Rosenberg, et al. (1981), "Relation of Benzodiazepine Use to the Risk of Selected Cancers: Breast, Large Bowel, Malignant melanoma, Lung, Endometrium, Ovary, Non Hodgkin's Lymphoma, Testis, Hodgkins Disease, Thyroid, and Liver," Am J Epidemiol 141: 1153–1160.

Wendy E. Solowey, et al. (1990) "Peripheral–Acting Benzodiazpines Inhibit the Growth of Human Malanoma cells Potentiate the Antiproliferative Activity of Recombinant Human Interferons" Journal of Interferon Research 10: 269–280.

John C. Reed, et al. (1995) " BCL–2: Prevention of Apoptosis As A Mechanism Of Drug Resistance," Drug Resistance In Clinical Oncology and Hematology 9:451–473.

John C. Reed (1995), "Regulation of Apoptosis by bcl–2 family proteins and its role in cancer and chemoresistance," Rapid Science Publishers: 541–546.

Hisako Hashimoto, et al. (1995) "Inhibition of Etoposide (VP–16)–induced DNA Recombination and Mutant Frequency by Bel–2 Protein Overexpression" Cancer Research 55: 4029–4035.

Burkhard Jansen, et al. (1998), bcl–2 antisense therapy chemosensitizes human melanama in SCID mice, Nature Medicine 4: 232–234.

Barry A. Bunin, et al. (1994) " The combinatorial sysnthesis and chemical and biological evaluation of a 1,4–benzodiazepine library," Proc. Natl. Acad. Sci. 91: 4708–4712.

Claus Braestrup et al. (1977) Specific benzodiazepie receptors in a rat brain characterized by high–affinity [3H] diazepam binding.

John F. Tallman, et al. (1980), " Receptors for the age of anxiety: Pharmacology of the Benzodiazepines" Science 207: 274–281.

Jie Yang, et al. (1997) " Prevention of Apoptosis by Bcl–2: Release of Cytochrome c from Mitochondria Blocked" Science Magazine 275: 1129–1136.

Moshe Gavish, et al. " Role of Peripheral–Type Benzodiazepine Receptors in Steroidogenesis" Clinical Neuropharmacology 20: 473–481.

Christine Teixeira, et al. (1995), " Estrogen Promotes Chemotherapeutic Drug Resistance by a Mechanism Involving Bcl–2 Proto–Oncogene Expression in Human Breast Cancer Cells", Cancer Research 55: 3902–3907.

Kleinerman, et al. (1984) "Diazepam use and Progression of Breast Cancer" Cancer Research 44: 1223–1225.

Nobuhiko Miyazawa, et al. (1998) "Assessment of the peripheral benzodiazapine receptors in human gliomas by two methods," Journal of Neuro–Oncology 38: 19–26.

Barry A. Bunin, et al. (1996), " Synthesis and Evaluation of 1, 4–Benzodiazepine Libraries" Methods in Enzymology 267: 448–465.

Candice E. Crooker, et al. (1996) " Benzodiazepine–Induced Inhibition of Human Malignant Melonoma (M–6) Cell Growth," Anticancer research 16: 1259–1264.

Daniela M. Zisterer, et al. (1997) " Peripheral–Type Benzodiazpine Receptors" Gen. Pharmac. 3: 305–314.

Rupnow, et al. (1998) "Direct Evidence that Apoptosis Enhances Tumor Responses to Fractionated Radiotherapy" Cancer Research 58: 1779–1784.

Toshiyuki, et al. (1992), " bcl–2 Gene Transfer Increases Relative Resistance of S49.1 and WEHI7.2 Lymphoid Cells to Cell Death and DNA Fragmentation Induced by Glucocorticoids and Multiple Chemotherapeutic Drugs" 52: 5407–5411.

* cited by examiner

— ·· — — — —
0  6  9  12  15  18  21 (HOURS)

— — — — —
0  6  9  12  15  18  21 (HOURS)

1  2  3  4  5  6

●  ··  ·· ●
1  2  3  4  5

COMPOUND FOR SELECTIVE TREATMENT OF MALIGNANT CELLS BY INHIBITING CELL CYCLE PROGRESSION, DECREASING BCL2, AND INCREASING APOPTOSIS

This patent application, filed by applicants Dr. Sydney Spector and Dr. Neil G. Spector, for a "A Compound for Selective Treatment of Malignant Cells by Inhibiting Cell Cycle Progression, Decreasing Bcl2, and Increasing Apoptosis" claims benefit of the filing date of Provisional Application Ser. No. 60/100,217, filed Sep. 14, 1998.

FIELD OF THE INVENTION

The present invention relates to compounds used in the treatment of cancer. More specifically, the present invention relates to a class of benzazepines which can be used for the treatment of cancers, including breast, prostate and glial cell cancer.

BACKGROUND OF THE INVENTION

Cancer is the second leading cause of death in the United States. In 1998, 564,800 Americans are expected to die of cancer (American Cancer Society). The National Cancer Institute estimates overall annual costs for cancer to be $107 billion. Thirty-seven billion dollars per year is spent in direct medical costs, with over half of the direct medical costs directly related to treatment of breast, lung, and prostate cancers.

Breast cancer is the second leading cause of cancer death in women, and the leading cause of cancer death among women age 40 to 55. In 1998, about 43,900 people (both men and women) are expected to die from breast cancer.

Chemotherapy is a common treatment for breast cancer, and a combination of anticancer drugs has proven more effective than a single drug. The effects of most chemotherapeutic agents are most profound on rapidly growing cells, such as cancer cells, although few agents have been found that exhibit a selective toxicity to cancer cells alone. The commonly known side effects of chemotherapy arise due to the cytotoxic effects of chemotherapeutic agents on normal cells.

The most commonly used chemotherapy combinations are cyclophosphamide, methotrexate, and fluorouracil (CMF) and cyclophosphamide, doxorubicin (Adriamycin), and fluorouracil (CAF). Recent data suggests that paclitaxel may also be useful for breast cancer treatment. Chemotherapy usually lasts three to six months and is given in cycles, with each period of treatment followed by a recovery period. The side effects of chemotherapy depend on the type of drugs, the amount taken, and the length of treatment. Typical side effects may include nausea and vomiting, loss of appetite, loss of hair, mouth sores, and changes in the menstrual cycle. Because chemotherapy can damage the blood-producing cells of the bone marrow, patients may have low blood cell counts, which can result in an increased chance of infection (due to a shortage of white blood cells), bleeding or bruising after minor cuts or injuries (due to a shortage of blood platelets), and fatigue (due to low red blood cell counts). Potential permanent complications of chemotherapy, particularly in older women, include premature menopause and infertility. Premature menopause may contribute to the development of osteoporosis and coronary artery disease, due to failure of the ovaries to produce estrogen. Adriamycin (doxorubicin) may cause permanent heart damage, so the dose of this drug must be carefully controlled. Very rarely, certain chemotherapeutic drugs may cause acute myeloid leukemia (AML) years after treatment.

Radiation therapy may be used to reduce the size of a tumor before surgery or to destroy cancer cells remaining in the breast, chest wall, or underarm area after surgery. The main side effects of radiation therapy are swelling and heaviness in the breast, sunburn-like skin changes in the treated area and possibly fatigue, but these changes to the breast tissue and skin usually go away in 6–12 months.

Another approach to treating breast cancer is to block the effect of estrogen or lower estrogen levels, often by the antiestrogen drug tamoxifen (Nolvadex). It is taken daily in pill form, for at least two years and usually for five years. Some studies have shown a slight increase of early stage endometrial cancer among women taking tamoxifen, with the risk increasing if the drug is taken for more than five years.

Megestrone (megace) is another drug used for hormonal treatment of advanced breast cancer, usually for women whose cancers do not respond to tamoxifen. Progestins (produced in the ovaries) or androgens (male hormones) also may used to treat advanced breast cancer. Side effects include fluid retention (progestin) and development of masculine characteristics (androgens).

Oophorectomy (surgery to remove the ovaries) may be used in pre-menopausal women to eliminate the body's main source of estrogen.

Prostate cancer is the second leading cause of cancer death in men. In 1998, 39,200 men are expected to die of prostate cancer in the United States. Recent advances in prostate cancer research include the discovery of a gene linked to prostate cancer, HPC1.

Treatment for prostate cancer follows a similar course to that taken in the treatment of breast cancer. Chemotherapy and hormone therapy figure prominently in the therapy regimen.

Chemotherapy, although helpful for decreasing the number of cancerous cells, has proven to be less satisfactory at producing remission from cancer than had been anticipated. The side effects of chemotherapy have made long-term treatment an unpleasant and harmful alternative. Furthermore, drug resistance to chemotherapeutic agents is common. A safe, effective chemotherapeutic agent, particularly one which could be combined with the chemotherapeutic agents presently available, would increase effectiveness of chemotherapy, while decreasing treatment time and decreasing the potential for the development of serious side effects.

SUMMARY OF THE INVENTION

The present invention relates to a novel class of benzazepine, exemplified by 2-amino-9-chloro-7-(2-fluorophenyl)-5H-pyrimido[5,4-d][2]benzazepine (BBL22), and a method of using these compounds for the treatment of cancer, particularly breast and prostate cancer.

The present invention provides benzazepine compounds of formula (I)

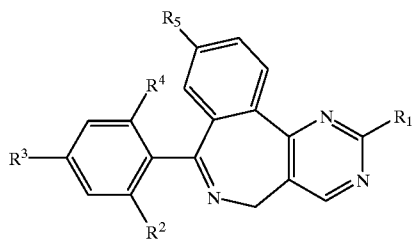

wherein:
R1 is an amino or an alkyl group, optionally substituted with at least one C1–C6 alkyl group;
R2 is H or halogen;
R3 is H, halogen, hydroxyl group, or alkyl group;
R4 is H or halogen;
R5 is halogen;
and salts thereof. In certain embodiments, R5 is fluorine. In certain embodiments, R1 is an amino group. In certain embodiments, R2 is fluorine. In certain embodiments, R5 is chlorine. In a preferred embodiment, R1 is an amino group, R2 is fluorine, and R5 is chlorine.

In the method of the present invention, BBL22 is administered parenterally, orally, topically, intravenously, or by other means to inhibit growth of cancer cells.

BBL22 and related compounds can be used to selectively arrest cancer cells in G2/M phase. BBL22 can therefore be used to selectively inhibit cancer cell growth for the treatment of cancer.

BBL22, or analogs thereof, are administered either as an independent chemotherapy or in combination with other chemotherapeutic agents to reduce tumor size and eradicate cancerous cells. BBL22, or analogs thereof, can also be administered in conjunction with single-dose or fractionated radiotherapy for the treatment of solid tumors.

BBL22 can be used to decrease cellular levels of Bcl-2. The effect of BBL22 on Bcl-2 levels has important therapeutic and research uses. BBL22 and functionally related compounds can be used to decrease Bcl-2 levels to investigate cell cycle control mechanisms. BBL22 and functionally related compounds can be used to decrease Bcl-2 levels to reduce drug resistance to other chemotherapeutic agents. Furthermore, BBL22 can be used in conjunction with other chemotherapeutic agents to inhibit cancer cell growth for the treatment of cancer.

BBL22 can be used for the purpose of screening other pharmaceutical agents for therapeutic effect in the treatment of cancer. Use of labeled BBL22 in competitive binding assays provides a method for high-throughput screening of compound libraries for target compounds with similar activity to that demonstrated for BBL22.

BBL22 can also be used for prevention of cancer, particularly in individuals who are determined to have an increased risk, due to genetic of environmental factors, for the development of cancer.

BRIEF DESCRIPTION OF THE DRAWINGS

FIG. 1 illustrates the results of cell cycle analysis performed on MCF 7 cells.

FIG. 3 illustrates the effect of BBL22 treatment of MCF7 cells on cyclin B. In FIG. 3b, lane 1 represents cyclin B levels in treated cells harvested at 30 minutes. Lane 2 represents cyclin B levels in treated cells harvested at 60 minutes, and lane 3 represents cyclin B levels in treated cells harvested at 120 minutes post-treatment. Lanes 4–6 represent untreated cells harvested at 30 minutes, 60 minutes, and 120 minutes, respectively.

FIG. 5 illustrates BBL22 localization to the nucleus of tumor cells, as indicated by fluorescence microscopy following fluorescent antibody treatment. MCF7 (malignant breast cell) and MCF10A (non-malignant breast epithelial cell) were treated or untreated with BBL22. Cells were then stained with anti-BZD (benzodiazepine) antibody, followed by secondary goat-antirabbit rhodamine-conjugated antibody.

DETAILED DESCRIPTION OF THE PREFERRED EMBODIMENTS

Figure 1A:
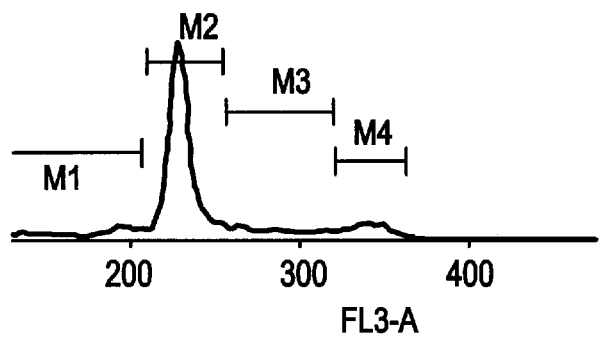
FIG. 1a illustrates the cell cycle results for untreated control MCF 7 cells.

The present invention seeks to overcome shortcomings inherent in the prior art by identifying a novel class of benzazepines which are non-toxic to nonmalignant cells, yet effective for inhibiting the growth of malignant cancer cells. It is important to an understanding of the present invention to note that all technical and scientific terms used anywhere herein, unless otherwise defined, are intended to have the same meaning as commonly understood by one of ordinary skill in the art; that techniques employed herein are also those that are known to one of ordinary skill in the art, unless stated otherwise; and that publications mentioned herein are incorporated by reference.

Benzodiazepines have been classified according to their interactions with two distinct binding sites. The most extensively studied group of BZDs bind a central-type receptor whose distribution is restricted to the brain and is associated with γ-aminobutyric acid (GABA) regulated chloride channels. The therapeutic anxiolytic, muscle relaxant, and anticonvulsive effects associated with BZDs, such as diazepam and clonazepam, are mediated through central-type receptors (Braestrup and Squires, 1977. Tallman, 1980). A second class of BZDs, the peripheral-acting BZDs, are characterized by their affinity for peripheral binding sites (PBRs), which are ubiquitously expressed on the outer mitochondrial membrane of peripheral tissues, as well as in glial cells in the brain. The expression of PBRs is especially high in steroidogenic organs. PBRs have been postulated to play a role in several functions, including cell proliferation, respiration, and steroidogenesis (Gavish and Weizman, 1997). Recent studies suggest that the peripheral binding sites consist of a complex that spans the inner and outer mitochondrial membranes and includes not only a BZD binding subunit, but also the voltage-dependent anion channel and adenosine nucleotide transporter of the outer and inner mitochondrial membranes, respectively. Interestingly, PBRs are expressed in a variety of human tumors, such as ovarian, colon, and breast, at higher density than that found in normal tissue (Miyazawa et al.).

Although PBR ligands have been shown to exert antiproliferative and prodifferentiative effects in animal tumor cells, the biological activity of these compounds does not correlate well with their binding affinity for PBR, indicating a questionable role for PBR in mediating these effects (Zisterer et al., 1998). PBR ligands such as diazepam, PK11195, and Ro5-4864, for example, have been shown to inhibit cell growth in a variety of cell lines, including mouse thymoma cells, rat C6 glioma, and mouse neuro-2A neuroblastoma cells. However, these compounds appear to arrest cell division in the G1 phase, and appear to do so without specifically interacting with the peripheral-type benzodiazepine binding site (Zisterer et al.) Ro5-4864 and related peripheral-type benzodiazepine agonists have been found to inhibit human melanoma cell growth, but a lack of correlation between binding affinities and antiproliferative potencies of these compounds suggests that a site other than a classical peripheral-type benzodiazepine receptor is involved (Solowey et al., 1990).

Except for studies showing that selected peripheral-acting BZDs enhanced nerve growth factor-induced expression of c-fos in rat PC12 pheochromocytoma cells, relatively little is known about the signaling pathway transducing the biological effects of peripheral-acting BZDs. Anderson et al. (1981) have found that diazepam appears to block mitosis by inhibiting the deviation of centrioles in prometaphase. Clarke and Ryan (1980) reported that benzodiazepines block non-differentiating NIH 3T3 cells in pre-S phase, while the same concentrations induce differentiation in Friend cells.

Recent epidemiologic studies have linked chronic diazepam use with a reduced risk of aggressive breast tumors. Findings indicate that chronic diazepam use correlates with smaller sized primary tumors and reduced incidence of lymph node involvement. In a case-control study of 280,000 women conducted at the National Cancer Institute, Fraumeni and colleagues found that those women taking diazepam had less aggressive breast cancers as reflected by smaller sized primary tumors and a reduced incidence of lymph node involvement (Kleinerman et al., 1984). A similar protective effect of BZDs was demonstrated in a case-reference study from the Southern California Kaiser Permanente Medical Group, where diazepam use was found to be associated with a reduced risk of breast cancer (Ziel et al.).

Not all peripheral-acting BZDs exert antiproliferative effects on cancerous cells, however. The peripheral-acting BZDs known as Ro5-4864, Ro5-515, Ro23-4566, Ro22-9395, and Ro22-9370 (Hoffman-LaRoche Pharmaceuticals) were found to have no inhibitory effect on the growth of breast cancer cells. Similarly, the high affinity PBR ligand PK11195, an isoquinoline carboxamide derivative, exhibited no inhibitory effect on cancerous breast epithelial tissue cell division. Other compounds tested and found to have no effect on inhibition of growth of malignant breast tissue cells include diazepam, clonazepam, Ro22-3792, Ro5-6900, Ro11-6896, Ro7-3371, Ro5-5120, Ro5-3464, and Ro7-5520 (Hoffman-LaRoche Pharmaceuticals).

In the present invention, a peripheral-acting benzazepine, BBL22 (2-amino-9-chloro-7-(2-fluorophenyl)-5H-pyrimido [5,4-d][2]benzazepine), has been demonstrated to inhibit cell cycle progression in malignant, but not non-malignant, breast and prostate tissue. Furthermore, BBL22 has been shown by the inventors to decrease levels of the cellular anti-apoptotic protein Bcl-2.

BBL22 is an off-white compound crystallized in ethanol/dichloromethane with a melting point of 245–248 degrees C. It is insoluble in water and alkali, and slightly soluble in acids. Synthesized as a potential antidepressant, BBL22 was subsequently found to have no therapeutic use. Only recently has the therapeutic utility of the compound, as described by the present invention, been discovered.

For the treatment of cancer, and the inhibition of Bcl-2, the present invention provides benzazepine compounds of formula (I)

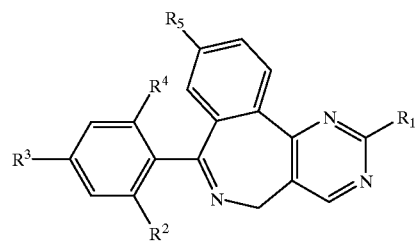

wherein:
R1 is an amino or an alkyl group, optionally substituted with at least one C1–C6 alkyl group;
R2 is H or halogen;
R3 is H, halogen, hydroxyl group, or alkyl group;
R4 is H or halogen;
R5 is halogen;
and salts thereof. In certain embodiments, R5 is fluorine. In certain embodiments, R1 is an amino group. In certain embodiments, R2 is fluorine. In certain embodiments, R5 is chlorine. In a preferred embodiment, R1 is an amino group, R2 is fluorine, and R5 is chlorine.

Formula (I) is intended to embrace all possible isomers, including optical isomers, and mixtures thereof, including racemates.

As used herein, alkyl means linear or branched chain alkyl. Examples of suitable alkyl groups include methyl, ethyl, isopropyl and isobutyl groups.

Halogen includes fluorine, chlorine, bromine and iodine. Preferably halogen will be fluorine or chlorine.

The preferred embodiment of the compound of the present invention is BBL22, a compound of Formula (II):

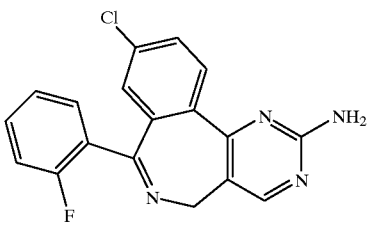

Benzodiazepine synthesis has been described in detail in U.S. Pat. No. 3,516,988 (Schmitt), U.S. Pat. No. 3,965,151 (Derieg et al.), U.S. Pat. No. 3,996,209 (Chase), U.S. Pat. No. 3,997,591 (Derieg et al.), U.S. Pat. No. 5,556,969 (Chambers et al.), U.S. Pat. No. 5,597,915 (Chambers et al.), and U.S. Pat. No. 4,377,522 (Branca et al.). In addition, the synthesis of benzodiazepine libraries has been described by Bunin et al. (Proc. Natl. Acad. Sci. 1994 and Methods Enzymol. 1996).

Methods for the synthesis of tricyclic benzazepine structures are described in detail by Gronwald (U.S. Pat. No. 5,010,074), Das (U.S. Pat. No. 4,752,645), Floyd (U.S. Pat. No. 4,902,684), and Floyd (U.S. Pat. No. 4,748,239); each incorporated herein by reference. A tricyclic intermediate is synthesized as in formula III, and subsequently reacted with guanidine as shown below to form the four ring compound of 2-amino-9-chloro-7-(2-fluorophenyl)-5H-pyrimido-[5,4-d][2]benzazepine (BBL22):

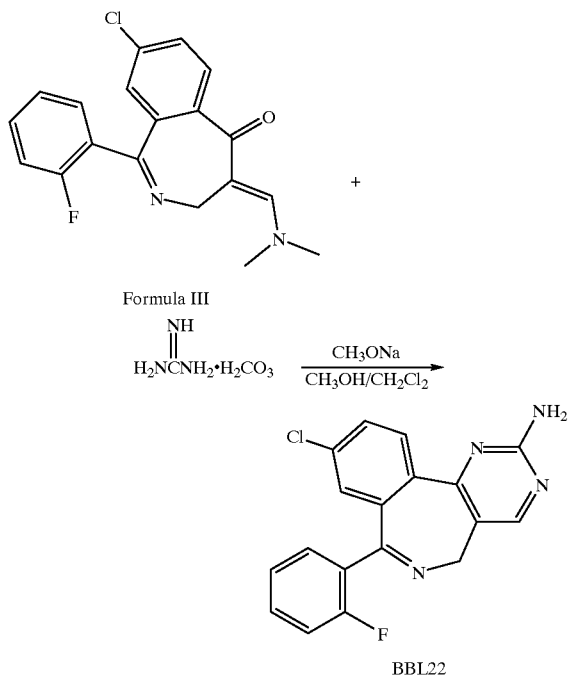

BBL22, and similar compounds of this basic formula, may be used as described below.

Inhibition of Proliferation of Malignant Cells In Vivo

In the method of the present invention, BBL22, and compounds having similar structure as described, are used for the prevention and treatment of cancer.

For prophylactic use, BBL22 is provided in doses of approximately 50 mg/kg to 250 mg/kg or more to decrease the levels of Bcl-2, an inhibitor of apoptosis. Bcl-2 is an integral membrane protein located mainly on the outer membrane of mitochondria. Overexpression of Bcl-2 has been shown to prevent cells from undergoing apoptosis. Bcl-2 has been shown to prevent mitochondrial membrane depolarization, an early event in apoptosis (Yang et al., 1997). By decreasing levels of Bcl-2, BBL22 provides a means for destroying cancer cells as they arise in the body. Researchers have known for some time that apoptosis of body cells occurs constantly and that its failure can contribute to cancer. Cancer develops after a cell accumulates mutations in genes that control cell growth and survival. When the mutations become irreparable, the cell usually kills itself rather than become a potential threat to other cells. However, some cells do not die but instead divide uncontrollably and metastasize, giving rise to malignancy. Expression of Bcl-2 has been correlated with inhibition of the suicide pathway known as apoptosis. By decreasing levels of Bcl-2, BBL22 encourages the cancer cell to proceed in the normal course of cell death.

For treatment, BBL22 is provided in doses of 50 mg/kg to 250 mg/kg or more to decrease the size of an established tumor or tumors. BBL22 has been demonstrated to have therapeutic effect by inhibiting the growth of tumors in both breast tissue and prostate tissue, as well as glial cell tumors. BBL22 is expected to have effect on other types of cancers which correlate with the expression of the protein Bcl-2, as exemplified by malignant melanoma. Melanocytes, for example, produce large amounts of Bcl-2. They are therefore less likely to undergo apoptosis when they become genetically damaged and are more likely, when malignant, to form aggressive tumors that spread rapidly. By inhibiting Bcl-2, BBL22 provides a method of encouraging malignant melanocytes to undergo apoptosis rather than continue to grow and divide uncontrollably.

Methods of administration of BBL22 can include, but are not limited to, oral administration, topical administration, intravenous administration, and parenteral administration. BBL22 can be administered orally by combining with a pharmaceutically acceptable carrier for administration in liquid, tablet, caplet, or capsule form. BBL22 can be provided for administration of dosages of varying concentration by administration of a combination of tablets, for example, providing doses appropriate to deliver a therapeutically effective concentration of BBL22 to the tumor site. Oral administration may include slow-release capsules, particularly for treatment of elderly or debilitated patients or children.

BBL22 can be administered intravenously at a concentration sufficient to produce a therapeutically effective concentration at the tumor site. BBL22 can also be administered by intramuscular injection or subcutaneous injection to provide a therapeutically effective concentration to the tumor site.

Figure 2:
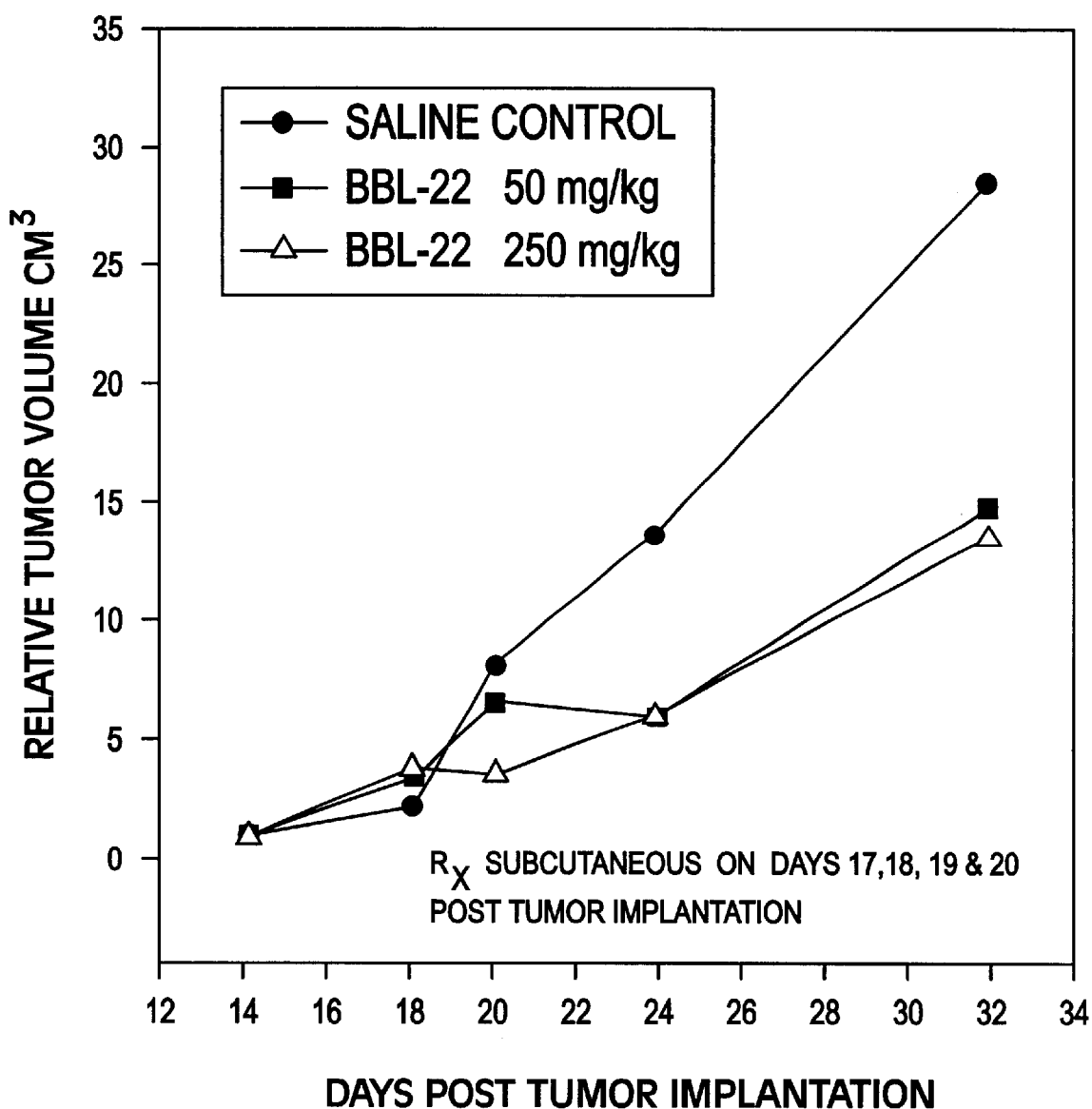
FIG. 2 illustrates the effect of BBL22 on PC-3 human prostate tumor xenografts into nude mice. Relative tumor volume, measured in cubic centimeters, is indicated on the vertical axis. The number of days post tumor implantation is indicated on the horizontal axis. Symbols in the box insert indicate untreated (saline) controls, mice treated with BBL22 at a concentration of 50 mg/kg after tumor implantation, and mice treated with BBL22 at a concentration of 250 mg/kg after tumor implantation.

A therapeutically effective concentration of BBL22 is readily determined by one of skill in the art using known methods. Typically, therapeutically effective amounts and concentrations are determined by the treating physician. As illustrated in FIG. 2, administration of 50 mg/kg or 250 mg/kg (dosage/body weight) results in a similar 50% reduction in tumor volume 32 days post tumor implantation in nude mice with dosages administered subcutaneously on days 17, 18, 19, and 20 post implantation. These data demonstrate that 50 mg/kg (dosage/body weight) is a saturating dose of BBL22. Doses of BBL22 that are less than 50 mg/kg are clearly in the therapeutically effective range, as demonstrated by the data in FIG. 2. In certain embodiments direct application of BBL22 to tumors and sites of tumors is utilized. In certain embodiments the therapeutically effective amount of BBL22 is less than the amount that is therapeutic when provided via a systemic route as the volume of treated tissue is less.

Figures 3A, 3B, 4:
FIG. 3a illustrates cyclin B steady state levels, as determined by immunoblot analysis. Cells were synchronized by aphidicolin block, and BBL22 treatment was initiated 1 hour after release from the block. Untreated controls are indicated by the upper row, while BBL22-treated samples are indicated by the lower row. Cell lysates were prepared at the times indicated beneath each row.
FIG. 3b illustrates cyclin B half-life in untreated cells and in cells treated with BBL22 1 hour following release from aphidicolin block. Cells were harvested at 30 minutes, 60 minutes, and 120 minutes after treatment.
FIG. 4 illustrates the effect of BBL22 on Bcl-2 protein levels in tumor cells. Lane 2 illustrates Bcl-2 protein levels in cells treated with 50 $\mu$M BBL22. Lane 3 represents protein levels in cells treated with 100 $\mu$M BBL22. Lane 4 represents protein levels in cells treated with 50 $\mu$M cyclosporine (an inhibitor of the mitochondrial transitional state in apoptosis). Lane 5 represents the Bcl-2 protein standard, and Lane 1 is untreated control.

As illustrated in FIG. 4, 50 µM or 100 µM BBL22 reduces the expression of Bcl-2 in tumor cells to a similar and multifold extent. Thus, the data in FIG. 4 demonstrate that the amount of BBL22 useful to significantly reduce Bcl-2 expression in tumor cells is less than 50 µM. One of ordinary skill in the art would be able to use the information provided in the present Specification, including FIG. 2 and FIG. 4, to determine an effective amount or concentration of BBL22 to administer for treating a tumor, especially a malignant tumor, in a subject. One of ordinary skill in the art would also realize that the amount or concentration of BBL22 may be reduced when treatment with BBL22 is coupled with another form of cancer therapy, including, but not limited to: chemotherapy, radiotherapy, surgical therapy, hormone therapy, and biological therapy.

Particularly in the case of tumors such as those found in malignant melanoma, BBL22 can be administered topically or subcutaneously to provide a therapeutically effective concentration to the tumor site. For the treatment of disseminated metastases, intravenous administration or oral administration to achieve systemic distribution is recommended.

BBL22 Used in Conjunction with Other Chemotherapeutic Agents

Breast and prostate cancer usually are treated, as are other forms of cancer, with a combination of surgical excision and radiation/chemotherapy. Chemotherapeutic agents used to treat breast cancer, for example, may include arabinosylcytosine (Ara-C), etoposide (VP-16), mitoxantrone hydrochloride, methotrexate, vinblastine, adriamycin, and cisplatinin (cis-platinum). None of these chemotherapeutic agents functions without exerting significant toxic effects on normal cells, producing serious side effects. Ara-C, for example, produces a decreased white blood cell counts, decreased platelets, anemia, hair loss, sore mouth and difficulty swallowing, diarrhea, and even damages the brain when administered at very high doses. Adriamycin produces similar side effects, with the addition of the inducement of heart problems and damage to veins. Methotrexate produces a folic acid deficiency, although the side effects of methotrexate may be ameliorated by administration of Leuvocorin.

Chemotherapeutic agents used for cancer treatment generally exert their effects on dividing cells. Agents such as cis-platinum, etoposide, and adriamycin produce DNA damage, usually by intercalating between the adjacent nucleotides to produce strand breakage. DNA damage during cell division would be expected to stimulate programmed cell death, or apoptosis. Since cancer cells are rapidly dividing and growing, these compounds are expected to inhibit those cells particularly. However, these agents do not distinguish between growing cancer cells and growing normal cells, and they therefore have a detrimental effect on normal cells, as well. For this reason, they are generally not administered for prolonged periods of time. Unfortunately, these agents are also not especially efficient at producing inhibitory effect on cancer cells, so chemotherapy administration must be repeated over a period of months.

BBL22 provides an enhancement of the effects of chemotherapeutic agents, leading to greater effectiveness and shorter treatment time, with a concomitant decrease in harmful side effects caused by prolonged chemotherapy. Jansen et al. (1998) have shown that bcl-2 antisense oligonucleotide treatment, which inhibits expression of Bcl-2, improves the chemosensitivity of human melanoma grown in severe combined immunodeficient (SCID) mice. When treated with dacarbazine alone, mean tumor weight was decreased without eradication of tumors in experimental animals, although dacarbazine is the single most effect chemotherapeutic agent for human melanoma. When treated with a combination of bcl-2 antisense oligonucleotide and dacarbazine, however, tumor size showed an even more significant decrease, with complete ablation of tumors in three of six animals.

Hashimoto et al. (1995) report that Bcl-2 has been shown to inhibit apoptosis induced by several anticancer agents. They demonstrated that overexpression of Bcl-2 is associated with reduction in VP-16 (etoposide)-induced genetic recombination, mutation, and cytotoxicity. Down-regulation of Bcl-2, therefore, would provide a means of enhancing the anti-cancer effects of VP-16.

Elevations in Bcl-2 protein levels achieved by gene transfer have been shown to protect a murine lymphoma and a leukemia cell line from apoptosis normally induced by a number of anticancer drugs, including dexamethasone, etoposide, methotrexate, cisplatin, cyclophosphamide, vincristine, and Ara-C (Miyashita et al., 1992). A number of other cancer cell lines have been shown to exhibit drug resistance to other chemotherapeutics in response to Bcl-2 expression, as well (Reed, *Hematol. Oncol.,* 1995).

Bcl-2 has been proposed to induce drug resistance by preventing the cell from translating the usual drug-induced damage into an effective apoptotic signal, thereby increasing survival time for injured cells (Reed, *Curr. Opinion Oncol.,* 1995). High levels of Bcl-2 expression have been correlated with low response rates, faster time to relapse, and shorter survival time for cancer patients (Id.). In MCF-7 cells, estrogen has been demonstrated to up-regulate Bcl-2 gene expression, while the anti-estrogen chemotherapeutic tamoxifen reduces Bcl-2 protein levels and causes those cells to be more sensitive to another chemotherapeutic agent, doxorubicin (Teixeira et al., 1995).

In the method of the present invention, therapeutic doses of BBL22 are combined with standard chemotherapy regimens for the treatment of breast and prostate cancer to enhance the effects on inhibition of malignant cells. In a preferred method, BBL22 is combined with cyclophosphamide, methotrexate, and fluorouracil (CMF) or cyclophosphamide, doxorubicin (Adriamycin), and fluorouracil (CAF) for the treatment of breast cancer.

BBL22 administration, can begin prior to administration of a second chemotherapeutic agent and be continued as a course of combined chemotherapy. Alternately, BBL22 administration may be concurrent with administration of a second chemotherapeutic agent. Combined chemotherapy, as herein described, however, is not limited to a combination of BBL22 and one other chemotherapeutic agent. BBL22 may be used in conjunction with a combination of one or more chemotherapeutic agents concurrently, or sequentially during the course of treatment.

BBL22 Used in Conjunction with Radiotherapy

Approximately 50% of cancer patients are treated with radiation therapy. Ionizing radiation may provide a very effective means of killing tumor cells of lymphoid and solid tumors. Studies have shown, however, that apoptosis plays an important role in responses to radiotherapy.

Rupnow, et al. (1998) demonstrated that increasing the sensitivity of tumor cells to die by apoptosis increases the efficacy of fractionate radiotherapy by reducing tumor cell clonogenic survival. Using an inducible c-Myc construct to regulate apoptosis sensitivity in Rat-1 fibroblasts, overexpression of Bcl-2 was demonstrated to increase tumor cell survival after fractionated radiotherapy. By increasing sensitivity of tumor cells to apoptosis, the efficiency of fractionated radiotherapy was increased. In the method of the present invention, therapeutic doses of BBL22 are administered prior to and during single-dose or fractionated radiotherapy to reduce tumor cell survival.

For the treatment of breast or prostate cancer, for example, BBL22 may be administered in anticipation of the onset of radiation therapy in order to sensitize cancer cells to the effects of radiation, which normally include nucleic acid damage leading to apoptosis.

Therapeutic doses of BBL22 are those described previously, which have been demonstrated to produce inhibition of Bcl-2. Therapeutic doses of radiation are known to those of skill in the art and are usually determined on an individual basis by the radiation oncologist.

Using BBL22 for the Treatment of Breast Cancer

BBL22 and related compounds can be used alone, or in combination with other chemotherapeutic agents, radiotherapy, and/or surgery for the treatment of breast cancer. BBL22 has been demonstrated to irreversibly arrest breast cancer cells in G2/M phase, while non-malignant breast epithelial cell growth was unaffected by BBL22. Continuous exposure to BBL22 was not required. BBL22, therefore, provides a chemotherapeutic agent with selectivity for cancer cells. By arresting the cell cycle of breast cancer cells, BBL22 inhibits the growth of tumor cells.

The decrease in cellular Bcl-2 resulting from treatment with BBL22 also provides a mechanism for augmenting the therapeutic effects of either chemotherapy, radiotherapy, or both. BBL22 has been demonstrated to decrease Bcl-2 levels. The chemotherapeutic agent tamoxifen has also been demonstrated to decrease Bcl-2 levels. This decrease in Bcl-2 levels has been shown to improve the therapeutic effects of other chemotherapeutic agents, such as doxorubicin.

Treatment with BBL22 to inhibit tumor growth can precede surgery in order to minimize tumor size and spread. Postoperative treatment can also be used in the chemotherapeutic regimen for treatment of inoperable tumors and inhibition of spread of tumor cells from the surgical site. In general, treatment with BBL22 can be used in association with or combined with surgery in order to minimize tumor size and to minimize tumor spread or potential spread to other locations, and to further enhance the effectiveness of the surgical procedure. What is intended by "in association with" is that the BBL22 treatment can be administered prior to, during, or after surgical resection of at least a portion of the tumor.

Therapeutic dosages of BBL22 for the treatment of breast cancer will be determined by each patient's individual physician. The inventors have shown that the effects of BBL22 are dose responsive, and that safe and effective levels of BBL22 are similar to those levels of dosage previously used with the anti-depressant diazepam. Certain dosages of diazepam include, but are not limited to: from 1 mg to 10 mg and from once to four times daily or as tolerated.

Using BBL22 to Treat Prostate Cancer

BBL22 provides a preoperative treatment to reduce tumor size and reduce the possibility of metastasis prior to surgical removal of a tumor. BBL22 also provides a postoperative treatment for inoperable tumors and for migrating cells which might leave the surgical site and establish new tumors at distance sites in the body. Migrating cells would be growth-arrested in G2/M phase, making them unable to grow and divide to produce a new tumor at a new site.

BBL22 also provides a chemotherapeutic agent which can be used alone, or in combination with other chemotherapeutic agents, to reduce tumor clonogenic survival. The effect of BBL22 on tumor cell growth provides a benefit without other chemotherapeutic treatment. The effect of BBL22 on Bcl-2 levels provides the added benefit, however, of making the tumor cells more susceptible to the effects of other chemotherapeutic agents. Combination therapy provides a therapeutic regimen which is more effective and requires a shorter course of treatment, with fewer side effects, than conventional chemotherapy.

BBL22 can also be used in combination with radiotherapy to increase the effects of radiation treatment on tumor clonogenic survival. Cells arrested in G2/M phase, with decreased levels of Bcl-2, are more susceptible to the damaging effects of radiation, particularly the effects on cellular DNA.

Using BBL22 for the Treatment of Brain Tumors

A high-grade human glioma cell line has demonstrated the same growth arrest in G2/M phase as that shown in breast epithelial cancer cells and prostate cancer cells. BBL22 can be used to treat brain tumors as a single chemotherapeutic agent, or in conjunction with other chemotherapeutic agents.

BBL22 can also be used in conjunction with radiotherapy regimens for the treatment of brain tumors. BBL22, or related compounds based on its structure, can be used prior to surgical excision of a brain tumor to decrease tumor size and decrease metastatic potential. BBL22 can also be used postoperatively to arrest growth of tumor cells which were not surgically removed. Furthermore, BBL22 provides a therapeutic agent for inhibiting growth of cells which may migrate from the tumor site or become established in the surgical incision to produce new tumors.

Treatment of Other Solid Tumors and Hematologic Cancers

Cell cycle analysis has demonstrated that a number of solid tumor cells and hematologic cancer cells, such as lymphomas, respond to BBL22 in the same manner as breast cancer cells. Use of BBL22 for the treatment of cancer is therefore not limited to the specific examples herein described. BBL22 can be used for the treatment of both solid tissue tumors and hematologic cancers. Methods of use as described for breast and prostate cancer are preferred methods for other tumor types, as well. Individual treatment regimens will be determined by the cancer patient's physician, however, as is the case with any chemotherapeutic treatment.

BBL22 Treatment During and Immediately Following Surgery to Reduce Survival and Growth of Cells at the Surgical Site and Sites Distant to the Surgical Site Surgical removal of tumors often provides a means by which tumor cells may be released from the tumor to migrate to distance sites through the circulation. Tumor cells sloughed off during surgery or temporarily attached to surgical instruments may become established at the site of the surgical incision, as well. At the site of the surgical incision, increased circulation and growth factors produced in response to the injury provide an ideal environment for tumor cell growth. Particularly during laparoscopic surgery, tumors have been reported to become established at the site of the surgical incision due to implantation and growth of cells which were released from the tumor mass during the surgical resection.

Administration of BBL22 in association with surgery (meaning prior to, during, and/or immediately after surgery) inhibits growth of tumor cells, barring them from forming an established tumor at the surgical resection site or at a site distance from the surgical site, while leaving the normal cells to grow and divide appropriately to aid in wound healing.

BBL22 can be administered orally prior to surgery, by providing the subject with tablets, capsules, or liquid preparations containing the compound. Such pharmaceutical preparations are well known to those of skill in the art. BBL22 can also be administered intravenously prior to, during, or immediately after surgery to provide effective concentrations at the resection site and at distant sites. BBL22 can also be administered locally by catheterizing the tumor bed following tumor excision and providing BBL22 in fluid which bathes the tumor bed as it is slowly dispensed through the catheter (a "drip") to control residual tumor cell growth (microscopic residual disease).

Using BBL22 to Screen Libraries for Compounds with Similar Therapeutic Value

Mimetics are compounds that can mimic the critical features of the molecular recognition process of a molecule and reproduce the action of the compound. A mimetic is expected to permit molecular interactions similar those of the natural molecule. While maintaining the functionalities and relative side-chain positions of the parent molecule, mimetics may even have improved pharmacokinetics in comparison with the parent. Morphine, for example, is a non-peptide peptidomimetic that mimics the opioid peptides.

Bunin, for example, has described solid-phase synthesis of 1,4-benzodiazepines to create a small-molecule library. These benzodiazepines are synthesized on a solid support by connecting three basic building blocks. After attachment of 2-aminobenzophenone hydroxyl or carboy derivatives to the support using an acid-cleavable linker, [(4-hydroxymethyl) phenoxyacetic acid], the N-protecting group is deblocked (using piperidine/DMF), and the weakly nucleophilic amine is acylated with an α-Fmoc-protected amino acid fluoride, using 4-methyl-2,6-di-tert-butylpyridine as an acid scavenger. Fmoc deprotection, followed by treatment with 5% acetic acid in DMF, produces cyclization to the intermediate lactam. Alkylating agents are then used, followed by cleavage of the new benzodiazepine from the solid support by aqueous acid.

Methods for producing benzodiazepine derivatives have also been described in U. S. Pat. No. 3,965,151 (Derieg et al.), U.S. Pat. No. 3,516,988 (Schmitt), U.S. Pat. No. 3,997,591 (Derieg et al.), U.S. Pat. No. 4,377,522 (Branca et al.) U.S. Pat. No. 3,996,209 (Chase), and U.S. Pat. No. 5,556,969 (Chambers et al.), incorporated herein by reference.

In the method of the present invention, compounds are screened for use as chemotherapeutic agents based upon their competitive inhibition of binding of BBL22 within the cell. In a preferred screening method, cell cultures are established using cell lines exemplified by MCF7 (a human mammary carcinoma cell line) and MDA-MB-468 (a breast cancer cell line). Fluorescent-labeled BBL22 is added to cell cultures in conjunction with an excess of target compound. A potentially useful target compound is identified as a compound which inhibits the binding of BBL22 to its target site, thereby causing BBL22 to remain unbound. Inhibition of BBL22 is indicated by the absence of fluorescent staining to nuclei of malignant cells treated with BBL22 and a target compound, as compared to fluorescence stained nuclei of malignant control cells treated with BBL22 alone. This technique may also be used in high-throughput screening using microtiter plates.

EXAMPLES

Peripheral-acting BZDs designated with the prefix "Ro" were provided by Hoffman-LaRoche Pharmaceuticals. Diazepam and PK11195 were purchased from Sigma Chemical Company. BBL22 was also provided by Hoffman-LaRoche, as Ro-22-2038.

MCF7 (a human mammary carcinoma cell line) and MCF10A (human breast epithelial) cells were cultured in Eagle's Minimum Essential Medium (EMEM), containing non-essential amino acids, 2 mM L-glutamine, 2 mg/ml bovine insulin, 10% heat inactivated fetal calf serum (FCS) and penicillin-streptomycin. MDA-MB-468 (a breast cancer cell line) cells were grown in L-15 medium containing 10% heat inactivated FCS. HS478t cells were grown in Dulbecco's modified Eagle's medium (DMEM) supplemented with 10% heat inactivated FCS. BT474 cells were grown in RPMI 1640 medium containing 10% heat inactivated FCS and penicillin/streptomycin. HST578BST cells were grown in DMEM supplemented with 10% heat inactivated FCS. All cells, except MDA-MB-468, were cultured in a humidified incubator at 37° C. with 5% $CO_2$. MDA-MB-468 cells were cultured without supplemental $CO_2$.

Protein electrophoresis and immunoblot analysis were performed according to standard protocols. Briefly, cells were harvested and lysed in buffer containing 20 mM HEPES (pH 8.0), 0.42 M NaCl, 1.5 mM $MgCl_2$, 0.2 mM EDTA, 0.5 mM DTT, 0.5 mM PMSF, and 25% (v/v) glycerol. Protein concentrations were determined by the Bradford method, and equal amounts of protein were run on a 10% SDS-polyacrylamide gel under reducing conditions. After electrophoresis, proteins were transferred to an Immobilon-p membrane and consistency of loading was confirmed by Ponceau S staining. The membrane was blocked for 1 hour with Tris-buffered saline (pH 7.4) containing 150 mM NaCl and 5% (w/v) lowfat milk (TBS) and subsequently incubated for 1 hours at room temperature with an anti-human cyclin B1 monoclonal antibody (Upstate Biotechnology, Lake Placid, N.Y.) at a 1:3000 dilution in TBS containing 0.2% (v/v) Tween 20 (TBST). Blots were subsequently washed three times in TBST and incubated with a goat anti-mouse horseradish peroxidase-conjugated antibody (1:5000 dilution in TBST). Blots were visualized by enhanced chemiluminescence. Blots were subsequently stripped and reprobed with an anti-human p34cdc2 monoclonal antibody (Upstate Biotechnology) at a dilution of 1:3000 in TBS and visualized as described above.

Cell cycle synchronization was achieved by blocking cells in G1 phase after overnight incubation with 5 mg/ml aphidicolin. Cells were subsequently washed three times in phosphate-buffered saline (PBS) and recultured in aphidicolin-free medium. One hour following release from aphidicolin block, BBL22 was added to cells at a final concentration of 50 mM. Cells were harvested eighteen hours later, during G2/M phase. Harvested cells were washed three times in PBS, and cultured in leucine-free medium. [$^3$H]-leucine was added at 100 mCi/ml for 30 minutes. The culture was then washed three times in PBS, and recultured in isotope-free medium. Cells were harvested and lysed in RIPA buffer 50 mM Tris-HCl (pH 7.4), 150 mM NaCl, 15 mM Na deoxycholate, 1% (v/v) Triton X-100, 50 mM NaF, 0.5 mM $Na_2SO_4$, and 0.5 mM PMSF). Cell extracts were equalized for protein content and precleared with Protein A Sepharose beads. After overnight incubation at 4° C. in the presence of anti-human cyclin B monoclonal antibody (Upstate Biotechnology), Protein A Sepharose beads were added, and immunoprecipitated protein was prepared in SDS sample buffer, heated at 100° C. for 5 minutes prior to electrophoresis on a 10% SDS-polyacrylamide gel.

Cdc2 kinase activity was determined using an in vitro kinase kit (Upstate Biotechnology). Cell cycle analysis was performed by harvesting cells and fixing with 70% ethanol in PBS. Cells were then pelleted and resuspended in 0.5 ml PBS containing propidium iodide (50 mg/ml) and DNase-free RNase (100 mg/ml). Cells were analyzed in a FACStar Plus (Becton Dickinson, San Jose, Calif.).

BBL22 Irreversibly Arrests Breast Cancer Cells in G2/M Phase

Neoplastic and non-malignant breast cancer cells were treated with a number of either centrally-acting BZDs (i.e., diazepam), or high-affinity PBR ligands such as Ro5-4864 and the isoquinoline carboxamide derivative PK11195. A dose-response curve was established for each compound over a range of concentrations (50 pM to 1 mM). The growth regulatory effects of BZDs were highly stereospecific, as indicated by the fact that only BBL22 had any growth regulatory effect. At concentrations between 25 and 50 mM, BBL22 arrested breast cancer cell growth regardless of estrogen receptor (ER) status (Table 1). Furthermore, PBR binding affinity did not correlate with biological activity, since high affinity PBR ligands, such as Ro5-4864 and PK11195, showed no effect on breast cancer cell growth.

TABLE 1

| Cell Type | Estrogen Receptor | G2/M Arrest in Response to BBL22 |
|---|---|---|
| Human Breast Cancers: | | |
| MCF-7 | ER+ | ++++ |
| BT 474 | ER− | ++++ |
| MDA-MB-468 | ER− | ++++ |
| HBL 100 | ER− | +++ |
| HS578t | ER− | ++++ |
| Nonmalignant Breast Epithelium: | | |
| MCF10A | ER− | No |
| HS578BST | ER− | No |
| Murine Mammary Tumor: | | |
| DA3 | | ++++ |
| 4T1 | | ++++ |
| Cervical Carcinoma: | | |
| HeLa | | ++++ |

Non-malignant breast epithelial cell growth was unaffected by BBL22 (Table 1). The selectivity of BBL22 was demonstrated by treating two cell lines established from the same patient. HS578t and HS578BST represent a malignant and non-malignant breast epithelial cell line, respectively. As shown in Table 1, BBL22 inhibited growth of HS578t cells, but not HS578BST cells.

Figure 1B:
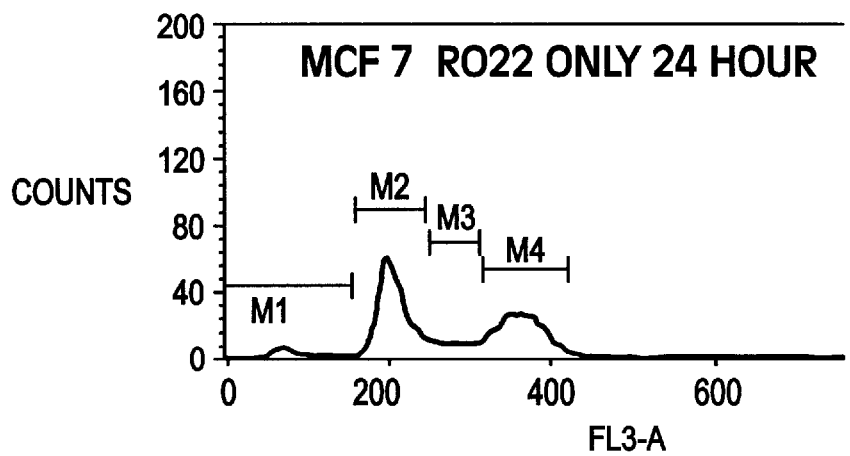
FIG. 1b illustrates the results of cell cycle analysis performed 24 hours after BBL22 treatment of MCF7 cells.
Figure 1C:
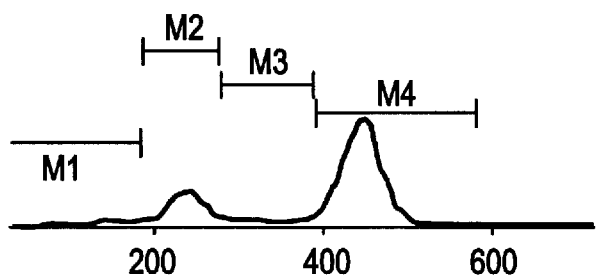
FIG. 1c illustrates the results of cell cycle analysis performed 72 hours after BBL22 treatment.

BBL22-induced growth regulation targets the cell cycle machinery. Using propidium iodide staining and flow cytometric cell cycle analysis, BBL22-treated breast cancer cells were demonstrated to arrest in G2/M phase of the cell cycle (FIG. 1). While the fraction of asynchronously dividing MCF7 cells in G2/M comprised only 9% of the total cell population, there was a 4-fold increase in the percentage of cells in G2/M after 24 hr of treatment with BBL22 (FIG. 1b). To determine whether the effects of BBL22 were reversible, cells were treated with BBL22 for 24 hours and then recultured in drug-free medium. Cell cycle analysis performed 72 hours later demonstrated that the percentage of cells blocked in G2/M increased to 70%, indicating the BBL22-induced cell cycle arrest was long-lived and did not require continuous exposure to the drug (FIG. 1c).

BBL22 Treatment Reduces Prostate Tumor Size

Nude mice were implanted with human prostate tumor. Seventeen days post-implantation, treatment with BBL22 was initiated. BBL22 was administered subcutaneously in doses of 50 mg/kg body weight and 250 mg/kg body weight, respectively. As illustrated in FIG. 2, by day 24 post tumor implantation and continuing, relative tumor volume was decreased by 50% in mice treated with either dose of BBL22. Thus, FIG. 2, demonstrates that BBL22 is therapeutic at less than 50 mg/kg, from 50 mg/kg to 250 mg/kg, and over 250 mg/kg body weight.

BBL22 Modulates Cyclin B Protein and p34cdc2 Phosphorylation State

Entry and progression through G2/M is regulated by cyclin B and its associated protein kinase p34cdc2. Activation of p34cdc2 kinase is dependent upon the formation of a complex with cyclin B. BBL22 affects cyclin B protein levels as well as maintaining p34cdc2 in a hyperphosphorylated, inactive state.

MCF7 cells were synchronized by arresting them during G1 phase with aphidicolin (50 mg/ml). Aphidicolin was washed out, releasing synchronized cells into the cell cycle. Cell cycle analysis performed at various time points thereafter demonstrated that MCF7 cells entered G2/M phase approximately 12 to 15 hours later. BBL22 was added 1 hour after release from the aphidicolin block while cells were in late G1 phase. Cell lysates were prepared at various time points thereafter and cyclin B steady state protein levels determined by immunoblot analysis (FIG. 3a). Lysates were equalized for protein concentration prior to electrophoresis. Steady state protein levels of cyclin B increased during late S phase and remained elevated during the transition from S phase to G2/M. In untreated controls, increased cyclin B steady state protein was transient, returning to baseline levels prior to the completion of mitosis at 21 hours. In contrast, cyclin B steady state protein levels remained persistently elevated in BBL22-treated cells and actually increased at 21 hours. Cyclin B protein expression was similarly regulated in other BBL-22 treated breast cancer cells. The normal periodicity of cyclin B protein levels during cell cycling in non-malignant breast epithelial cells was unaffected by BBL22.

Immunoblotting distinguishes between the inactive (phosphorylated) form of p34cdc2 and the active form, since the activated form is hypophosphorylated and therefore migrates faster on SDS-PAGE. As untreated controls progressed through mitosis, p34cdc2 was found primarily in its hypophosphorylated state. In contrast, the hyperphosphorylated form of the enzyme persisted in BBL22-treated cells.

Cyclin B Protein is Stabilized by BBL22

Proteolysis of cyclin B plays an important role in regulating the transition from metaphase to anaphase. Cyclin B is normally rapidly degraded by the ubiquitin-dependent proteasome. BBL22-treated cells demonstrated increased cyclin B protein half-life, indicating that BBL22 enhances cyclin B protein stability.

Breast cancer cells were synchronized as previously described. BBL22 was added to synchronized cells and pulse-chase radiolabeling was performed 15 hours later, when MCF7 cells were in G2/M. Cell extracts were equalized for protein content prior to immunoprecipitating cyclin B. In untreated controls, cyclin B protein exhibited a significantly shorter half-life than in BBL2-treated cells.

MCF7 cells were blocked in G1 phase using aphidicolin (50 mg/ml). After a 16 hour incubation, 85% of the cells were blocked in G1 phase, with greater than 95% viability, as determined by trypan blue exclusion. Aphidicolin was then washed out and cells were released into the cell cycle. Cell cycle analysis was performed at various time points thereafter. Synchronized MCF7 cells entered G2/M phase approximately 12 to 15 hours after their release into the cell cycle. BBL22 was added while synchronized cells were in late G1, approximately 1 hour after aphidicolin release. Cells were harvested and lysed at various time points following their release into the cell cycle. All samples were equalized for protein concentration prior to immunoblotting. As shown in FIG. 3a, cyclin B steady state protein levels increased transiently, returning to baseline levels as cells exited mitosis by 21 hours. In contrast, cyclin B protein levels remained persistently elevated and actually increased slightly at 21 hours in BBL22-treated cells. A similar effect of BBL22 on cyclin B steady state protein levels was observed in MDA-MB-468 breast cancer cells.

To investigate whether BBL22 was stabilizing cyclin B protein during mitosis, cyclin B half-life was determined in pulse-chase labeling experiments in untreated and BBL22-treated breast cancer cells. MCF7 cells were first synchronized and then released into the cell cycle as described previously. BBL22 was added 1 hour following release and pulse-chase labeling was performed 15 hours later, when cells were in G2/M phase. Cell extracts were equalized for protein concentration prior to immunoprecipitating with cyclin B. After pulse labeling with [$^3$H]-leucine and then chasing with "cold" leucine, cells were harvested at 30 minutes, 60 minutes, and 120 minutes. The unstable nature of cyclin B protein during mitosis was demonstrated by the absence of immunoprecipitated cyclin B from extracts of untreated cells (FIG. 3b). In contrast, cyclin B half-life increased significantly in BBL22-treated cells. The normal changes in cyclin B protein levels in nonmalignant MCF10A and HS578BST cells were unaffected by BBL22 treatment.

BBL22 Mediates Cell Cycle Arrest without Interacting with Peripheral Binding Receptors MCF7 cells were pretreated with the high affinity PBR ligand PK1 1195 for 6 hours at a concentration of 100 mM. Under these conditions, PBR binding sites have previously been shown to become saturated. Treatment with PK11195 alone had no effect on breast cancer cell growth. However, pretreatment with PK11195 also had no effect on BBL22-induced cell cycle arrest. Similar results were obtained when receptor sites were saturated with another high affinity PBR ligand, Ro5-4864, indicating that the effects mediated by BBL22 on malignant cells are not the result of BBL22 interacting with the peripheral binding receptors.

BBL22 Does not Affect the G2 DNA Repair Checkpoint

To rule out the possibility that BBL22 was exerting its effects through the G2 repair checkpoint, cells were pretreated with caffeine prior to adding BBL22. Pretreatment with caffeine produced no abrogation of BBL22 effects on cell cycling, indicating that the action of BBL22 is not associated with the G2 repair checkpoint.

Breast cancer cells were pretreated with caffeine (4 mM) for 30 minutes prior to adding BBL22. Under these conditions, caffeine has previously been shown to overcome g-irradiation induced G2 arrest. However, pretreatment with caffeine did not abrogate BBL22-induced G2/M arrest.

BBL22 Downregulates Bcl-b 2

Using immunoblot analysis as previously described, BBL22 was demonstrated to downregulate Bcl-2 protein levels in tumors (FIG. 4). Cyclosporine A (5 mM) has been shown to block apoptosis induced through changes in the mitochondrial membrane potential. Cyclosporine A, however, did not block BBL22-induced downregulation of Bcl-2.

Tumor cells were treated with 50 µM BBL22, 100 µM BBL22, 50 µM cyclosporine, or untreated. Bcl-2 protein was used as a standard during the immunoblotting procedure.

BBL22 is Translocated to the Nucleus in Malignant Cells

As shown in FIG. 5, BBL22 is translocated to the nucleus in malignant cells, but remains in the cytoplasm in normal cells. FIG. 5a illustrates the distribution of anti-benzodiazepine (anti-BZD) antibody labeled by binding of 2° goat-anti rabbit rhodamine-conjugated antibody in untreated MCF7 (malignant breast) cells used as control. As expected, labeled antibody is not noticeable. FIG. 5c illustrates the distribution of the same anti-BZD antibody in cells treated with 50 mM BBL22 for 24 hours. Notably, antibody distribution is primarily within the nucleus of the MCF7 cells. FIG. 5e illustrates distribution of anti-BZD antibody in MCF7 cells treated with BBL22 for 24 hours and subsequently washed prior to addition of drug-free medium. Antibody staining was performed 48 hours later. Labeled anti-BZD antibody appears prominently in the nuclei and particularly in the nuclear membranes. In contrast, anti-BZD staining of cells treated with an equivalent concentration (50 mM) RO5-4864 for 24 hours indicates no such distribution within the nuclei.

Figure 5A:
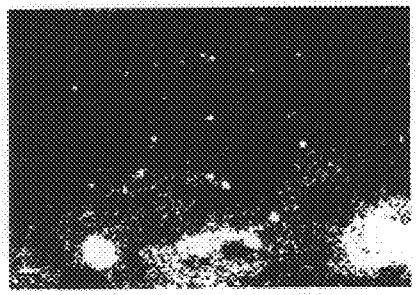
FIG. 5a is the untreated control for MCF7.
Figure 5B:
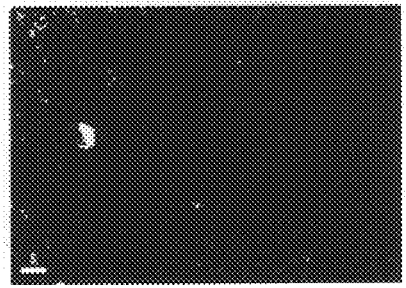
FIG. 5b is the untreated control for MCF10A.
Figure 5C:
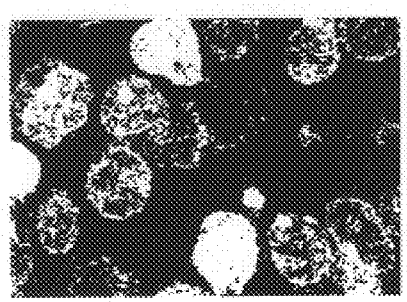
FIG. 5c illustrates MCF7 cells.
Figure 5D:
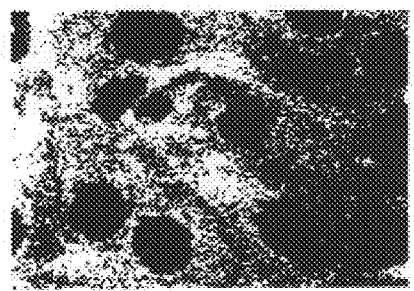
FIG. 5d illustrates MCF10A cells, treated with BBL22 (50 $\mu$M) for 24 hours.
Figure 5E:
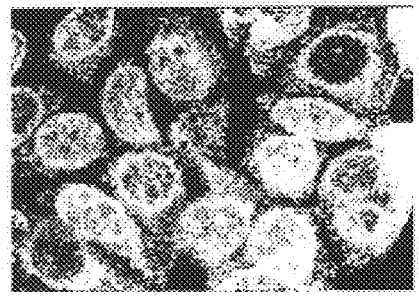
FIG. 5e illustrates MCF7 cells.
Figure 5F:
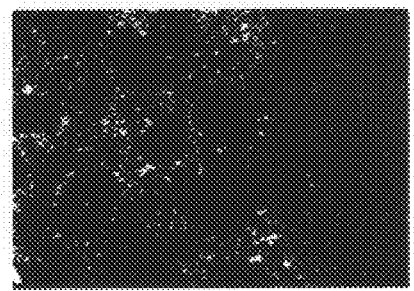
FIG. 5f illustrates MCF10A cells, treated for 24 hours, washed, continued on drug-free medium, and stained 48 hours later.
Figure 5G:
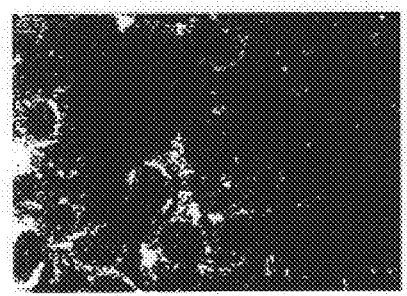
FIG. 5g illustrates MCF7 cells.
Figure 5H:
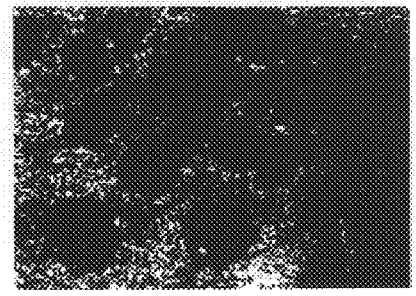
FIG. 5h illustrates MCF10A cells, treated with the benzodiazepine Ro5-4864 (50 $\mu$M) for 24 hours.

FIG. 5b illustrates anti-BZD staining of untreated MCF10A (non-malignant breast epithelial) cells. FIG. 5d illustrates MCF10A cells stained with anti-BZD antibody after 24 hour treatment with 50 mM BBL22. FIG. 5f illustrates MCF10A cells stained with anti-BZD antibody after 24 hour treatment with BBL22, followed by washing and replacement of medium with drug-free medium. Staining was performed 48 hours after replacement of medium. FIG. 5h illustrates anti-BZD staining after 24 hour Ro5-4864 treatment of MCF10A cells. Of significance is the fact that nuclear staining is not observed in FIG. 5b, FIG. 5d, FIG. 5f, or FIG. 5h; illustrating that BBL22 does not localize within the nucleus in non-malignant cells.

The following references, to the extent that they provide details supplementary to those set forth herein, are specifically incorporated herein by reference.

Anderson, et al. (1981), "Diazepam Induces Mitotic Arrest at Prometaphase by Inhibiting Centriolar Separation," *Nature* 291: 247–248.

Braestrup, C. and R. F. Squires (1977), "Specific Benzodiazepine Receptors in Rat Brain Characterized by High-affinity [3H] Diazepam Binding," *Proc. Natl. Acad. Sci. USA* 74: 3805–3809.

Bunin, et al. (1994), "The Combinatorial Synthesis and Chemical and Biological Evaluation of a 1,4-benzodiazepine Library," *Proc. Natl. Acad. Sci. USA* 91(11): 4708–4712.

Bunin, et al. (1996), "Synthesis and Evaluation of 1,4-benzodiazepine Libraries," *Methods Enzymol.* 267: 448–465.

Clark, G. D. and P. J. Ryan (1980), "Tranquilizers Can Block Mitogenesis in 3T3 Cells and Induce Differentiation in Friend Cells," *Nature* 287: 161–161.

Gavish, M. and R. Weizman (1997), "Role of Peripheral-type Benzodiazepine Receptors in Steroidogenesis," *Clin. Neuropharmacol.* 20(6): 473–481.

Hashimoto, et al. (1995), "Inhibition of Etoposide (VP-16)-induced DNA Recombination and Mutant Frequency by Bcl-2 Protein Overexpression," *Cancer Res.* 55(18): 4029–4035.

Jansen, et al. (1998), "bcl-2 Antisense Therapy Chemosensitizes Human Melanoma in SCID Mice," *Nature Med.* 4(2): 232–234.

Kleinerman, et al. (1984), "Diazepam Use and Progression of Breast Cancer," *Cancer Res.* 44: 1223–1225.

Miyashita, et al. (1992), "Bcl-2 Gene Transfer Increases Relative Resistance of S49.1 and WEHI7.2 Lymphoid Cells to Cell Death and DNA Fragmentation Induced by Glucocorticoids and Multiple Chemotherapeutic Drugs," *Cancer Res* 52: 5407–5411.

Miyazawa, N., et al. (1998), "Assessment of the Peripheral Benzodiazepine Receptors in Human Gliomas by Two Methods," *J. Neurooncol.* 38(1): 19–26.

Reed, J. C. (1995), "Bcl-2: Prevention of Apoptosis as a Mechanism of Drug Resistance," *Hematol Oncol Clin North Am* 9: 451–474.

Reed, J. C. (1995), "Regulation of Apoptosis by Bcl-2 Family Proteins and Its Role in Cancer and Chemoresistance," *Current Opinion in Oncology* 7: 541–546.

Rupnow, et al. (1998), "Direct Evidence That Apoptosis Enhances Tumor Responses to Fractionated Radiotherapy," *Cancer Res.* 58(9): 1779–1784.

Solowey, et al. (1990), "Peripheral-acting Benzodiazepines Inhibit the Growth of Human Melanoma Cell and Potentiate the Antiproliferative Activity of Recombinant Human Interferons," *J. Interferon Res.* 10: 269–280.

Tallman, et al. (1980), "Receptors for the Age of Anxiety: Pharmacology of Benzodiazepines," *Science* 207: 274–281.

Teixeira, et al. (1995), "Estrogen Promotes Chemotherapeutic Drug Resistance by a Mechanism Involving Bcl-2 Protooncogene Expression in Human Breast Cancer Cells," *Cancer Res* 55: 3902–3907.

Yang, et al. (1997), "Prevention of Apoptosis by Bcl-2: Release of Cytochrome c from Mitochondria Blocked," *Science* 275: 1129.

Zisterer, et al. (1998), "Antiproliferative Action of Pyrrolobenzoxazapine Derivatives in Cultured Cells: Absence of Correlation with Binding to the Peripheral-Type Benzodiazepine Binding Site," *Biochem. Pharmacol.* 55: 397–403.

What is claimed is:

1. A method of increasing a sensitivity of a cancer cell to a cancer treatment, comprising administering to said cancer cell an effective amount of a compound having the formula:

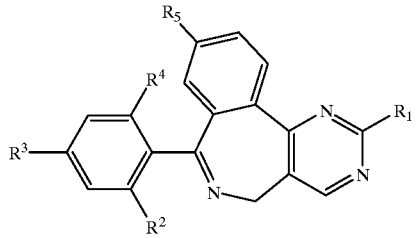

wherein
R1 is an amino or an alkyl group, optionally substituted with at least one C1–C6 alkyl group;
R2 is H or halogen;
R3 is H, halogen, hydroxyl group, or alkyl group;
R4 is H or halogen;
R5 is a halogen;
and salts thereof.

2. The method of claim 1, wherein R1 is amino, R2 is fluorine, and R3 is chlorine.

3. The method of claim 1, wherein said cancer treatment is chemotherapy.

4. The method of claim 1, wherein said cancer treatment is radiotherapy.

5. A method of inhibiting a chemotherapeutic drug resistance in a chemotherapeutic drug resistant cancer cell, comprising administering to said chemotherapeutic drug resistant cancer cell an effective amount of a compound having the formula:

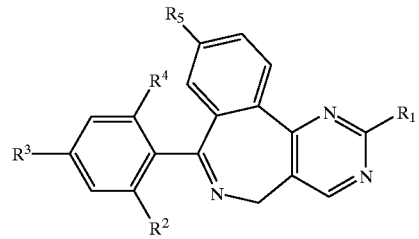

wherein
R1 is an amino or an alkyl group, optionally substituted with at least one C1–C6 alkyl group;
R2 is H or halogen;
R3 is H, halogen, hydroxyl group, or alkyl group;
R4 is H or halogen;
R5 is a halogen;
and salts thereof.

6. The method of claim 5, wherein R1 is amino, R2 is fluorine, and R3 is chlorine.

7. The method of claim 5, wherein said inhibiting step further comprises treating a tumor in a subject in need thereof.

8. A method for treating a tumor in a subject in need thereof, comprising: administering to said subject a therapeutically effective amount of a compound having the formula:

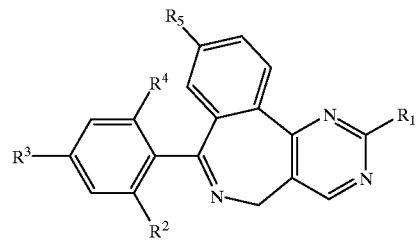

wherein
R1 is an amino or an alkyl group, optionally substituted with at least one C1–C6 alkyl group;
R2 is H or halogen;
R3 is H, halogen, hydroxyl group, or alkyl group;
R4 is H or halogen;
R5 is a halogen;
and salts thereof, wherein the tumor is selected from a group consisting of: a prostate cancer, a breast cancer, a malignant melanoma, a brain tumor, a cervical cancer and a hematologic cancer.

9. The method of claim 8, wherein R2 is fluorine and wherein R5 is chlorine or fluorine.

10. The method of claim 8, wherein R1 is the amino group, R2 is fluorine, and R5 is chlorine or fluorine.

11. The method of claim 8, wherein said compound is further defined as a 2-amino-9-chloro-7-(2-fluorophenyl)-5H-pyrimido-[5,4-d][2]benzazepine.

12. The method of claim 8, said tumor is the prostate cancer.

13. The method of claim 8, wherein said tumor is the breast cancer.

14. The method of claim 8, wherein said tumor is the malignant melanoma.

15. The method of claim 8, wherein said tumor is the brain tumor.

16. The method of claim 8, wherein said tumor is the hematologic cancer.

17. The method of claim 8, wherein said tumor is the cervical cancer.

18. The method of claim 8, wherein said administering step is via oral, topical, subcutaneous, intramuscular, intravenous, or parenteral routes.

19. The method of claim 8, wherein said administering step comprises administering said compound locally into the area of said tumor.

20. The method of claim 8, wherein said therapeutically effective amount is sufficient to reduce a volume of said tumor.

21. The method of claim 8, wherein said treating step further comprises administering said compound more than once.

22. The method of claim 8, wherein said treating step further comprises administering to said subject a cancer chemotherapeutic agent.

23. The method of claim 8, wherein said therapeutically effective amount of said compound is less than 50 milligrams per kilogram of body weight of said subject.

24. The method of claim 8, wherein said therapeutically effective amount of said compound is approximately 50 milligrams per kilogram of body weight of said subject to approximately 250 milligrams per kilogram of body weight of said subject.

25. The method of claim 8, wherein said therapeutically effective amount of said compound is more t an 250 milligrams per kilogram of body weight of said subject.

26. The method of claim 8, wherein said treating step further comprises a surgical resection of at least a portion of said tumor.

27. The method of claim 8, wherein said compound is administered into an area of said surgical resection.

* * * * *